Figure 1:
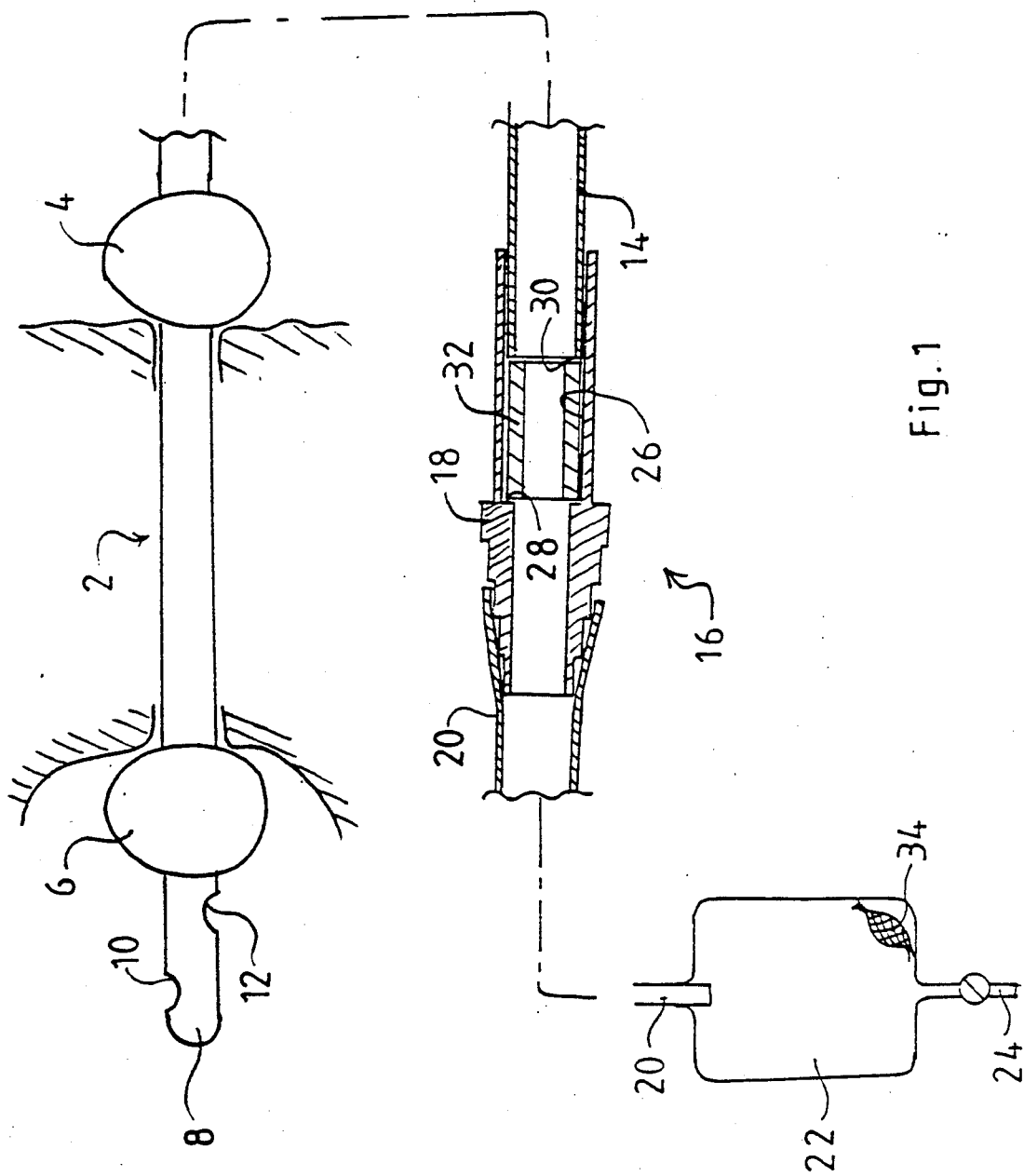

United States Patent [19]

Gilchrist

[11] Patent Number: 5,049,139
[45] Date of Patent: Sep. 17, 1991

[54] APPARATUS FOR ANTIMICROBIAL USE

[75] Inventor: Thomas Gilchrist, Ayr, Scotland

[73] Assignee: Giltech Limited, Ayr, Scotland

[21] Appl. No.: 465,146

[22] PCT Filed: Aug. 26, 1988

[86] PCT No.: PCT/GB88/00701
§ 371 Date: Feb. 23, 1990
§ 102(e) Date: Feb. 23, 1990

[87] PCT Pub. No.: WO89/01793
PCT Pub. Date: Mar. 9, 1989

[30] Foreign Application Priority Data

Aug. 29, 1987 [GB] United Kingdom ............... 8720502

[51] Int. Cl.⁵ .................................................. A61M 5/32
[52] U.S. Cl. ......................................... 604/265; 604/905
[58] Field of Search ................................... 604/27–29, 604/54, 265, 905; 128/912

[56] References Cited

U.S. PATENT DOCUMENTS 4,354,490 10/1982 Rogers ................................. 604/905
4,559,033 12/1985 Stephen et al. ..................... 204/265
4,564,361 1/1986 Akiyama ............................. 604/265
4,919,658 4/1990 Badia .................................. 604/265
4,933,178 6/1990 Capelli ............................... 604/265

FOREIGN PATENT DOCUMENTS 0042219 12/1981 European Pat. Off. .
0059694 9/1982 European Pat. Off. .
0140538 5/1985 European Pat. Off. .
2506162 11/1982 France .
8501210 3/1985 PCT Int'l Appl. .

Primary Examiner—Stephen C. Pellegrino
Assistant Examiner—Michael Rafa
Attorney, Agent, or Firm—Ratner & Prestia

[57] ABSTRACT

Apparatus for use in fluid flow lines to or from a living body in order to reduce the incidence or growth of bacteria comprising in the flow line a connecting member which includes water-soluble silver impregnated glass, whereby the glass undergoes slow dissolution with concomitant release of silver into the fluid. The silver has antibacterial or bacterial static properties.

10 Claims, 3 Drawing Sheets

APPARATUS FOR ANTIMICROBIAL USE

This invention relates to an antimicrobial composition for use in medicine. The invention also relates to a device for use in medicine, which embodies the said composition and to a method of inhibiting or combating infection.

The antimicrobial action of silver ions is well known as are pharmaceutical formulations containing silver salts as active principle. Perhaps the best known example of such materials is silver sulphadiazine. However, silver nitrate and silver allantoinate are also used as antimicrobials.

For protracted protection against infection it is desirable that the release of the silver ion be sustained over an extended period of time.

It is known that certain glasses, in which the usual glass former, silicon dioxide, of traditional glasses is replaced with phosphorus pentoxide as the glass former, are soluble in water and body fluids. The rate of dissolution is controlled largely by the addition of glass modifiers such as calcium and magnesium oxide. In simple terms, the greater the concentration of the modifier the slower is the rate of dissolution. The rates of dissolution which can be imparted to the lasses may range from minutes to months or even to several years. It is known to include in such compositions quantities of trace elements such as copper, cobalt and selenium which will be released from the glass as it slowly dissolves over the selected period of time.

The use of water-soluble glasses has been described for a variety of purposes in the literature. For example, UK Patent Specifications numbers 1,565,906, 2,079,152, 2,077,585 and 2,146,531 describe the gradual dissolution of the glasses as providing a means of controlled release of drugs, hormones, fungicides, insecticides, spermicides and other agents with which the glasses have been impregnated. The glasses are used for example in the form of an implant or bolus.

UK Patent Specification number 2,030,559 describes the use of selenium-impregnated water-soluble glass for providing controlled release of the selenium as a trace element into cattle and sheep, the glass being applied as a subcutaneous insert. UK Patent Specification number 2,037,735 also describes a subcutaneous implant of water-soluble glass, and in this case the glass is impregnated with copper; minor quantities of trace elements such as boron, arsenic, iodine, manganese, chromium, silver, gold and allium may also be included.

Water-soluble glass has also been proposed for use in prosthetics, for example in UK Patent Specification number 2,099,702, and for use in anticorrosive paints, as described in UK Patent Specification number 2,062,612. Further the literature provides for the use of such glasses in the controlled release of ferrous and ferric ions into the human or animal body by ingestion or implantation of the glass (UK Patent Specification number 2,081,703), and for the use of glasses in the controlled release of ions such as lithium, sodium, potassium, caesium, rubidium, polyphosphate, calcium and aluminium to patients by inclusion of the glass in a drip feed line (UK Patent Specification number 2,057,420).

According to the present invention there is provided apparatus for antimicrobial use in passage of fluid to or from a living body, the apparatus comprising a conduit for insertion into the body, a reservoir for fluid and a connector member for connecting said conduit to said reservoir external of the body, wherein said connector member includes a water-soluble glass impregnated with elemental silver or a compound of silver, said water-soluble glass defining at least a part of a passageway for fluid to flow between the reservoir and the conduit.

The apparatus of the present invention preferably contains the impregnated water-soluble glass at a site at which bacteria can be introduced or increased in number, and the bacteriostatic or bactericidal properties of the silver has the effect of containing or reducing the risk of infection in the body. The connector member may comprise a first portion having an end adapted for connection with said conduit and a second portion having an end adapted for connection with said reservoir, the first and second portions being releasably secured together to define a fluid passageway between the reservoir and the conduit and at least one of the first and second portions having an internal lining of said impregnated water-soluble glass. The internal lining may be retained between spaced shoulders on the first or second portion, so that when the portions are separated the lining is held in position until re-connection is made.

The connector member may be in the form of a fitting which connects together upstream and downstream tubing, each of the first and second portions of the connector being disposed at an end of the respective tubing. If it becomes necessary to disconnect the tubing remote from the patient, for example to replace a full reservoir of fluid drained from the patient with an empty one, or to replace an empty reservoir of fluid delivered to the patient with a full one, the connector can be broken and the silver reduces the danger of infection to the patient through ingress of bacteria.

The connector member may consist of or include a length of tubing, for example of plastics material, rubber or silicone rubber, in which the impregnated water-soluble glass is dispersed so that the silver is released from the tubing wall.

The reservoir may also contain impregnated water-soluble glass, especially in the case where fluid is being drained from the patient, for example in urine drainage systems. During collection of the urine in the reservoir in conventional systems bacteria multiply and there is a risk that they may migrate along the drainage tubing to the patient, thereby increasing the incidence of bacteria and producing urinary tract infection. Inclusion in the reservoir of an apertured container in which silver-impregnated water-soluble glass is disposed prevents the multiplication of bacteria in the reservoir and therefore reduces the infection risk. A preferable form of container has been found to be a flexible braided polyester sleeve closed at each end to form an elongate pouch and containing granules of the glass. This system also protects nursing staff, who are required to replace full reservoirs, and/or to drain off urine from full reservoirs, by preventing proliferation of bacteria in the urine.

The apparatus of this invention may be used for example in urine drainage systems, post-surgical drainage systems, cannula systems and renal and peritoneal dialysis systems.

The present invention also provides a connector member having an inlet and an outlet and having walling defining a through passageway for flow of liquid from the inlet to the outlet, at least a part of said walling being formed of water-soluble glass impregnated with elemental silver or a compound of silver.

The optimum rate of release of silver ions into an aqueous environment may be selected by circumstances and particularly by the specific function of the released silver. In some cases, the required rate of release may be such that all of the silver added to the system is released in a short period of hours or days and in other applications it may be that the total silver be released slowly at a substantially uniform rate over a period extending to months or even years. In particular cases there may be additional requirements, for example it may be desirable that no residue remains after the source of the silver ions is exhausted or, in other cases, where silver is made available it will be desirable that any materials, other than the silver itself, which are simultaneously released should be physiologically harmless. In yet other cases, it may be necessary to ensure that the pH of the resulting solution does not fall outside defined limits.

Typically the soluble glasses used in this invention comprise phosphorus pentoxide ($P_2O_5$) as the principal glass-former, together with any one or more glass-modifying non-toxic materials such as sodium oxide ($Na_2O$), potassium oxide ($K_2O$), magnesium oxide (MgO) and calcium oxide (CaO). The rate at which the silver-release glass dissolves in fluids is determined by the glass composition, generally by the ratio of glass-modifier to glass-former and by the relative proportions of the glass-modifiers in the glass. By suitable adjustment of the glass composition, the dissolution rates in water at 38° C. ranging from substantially zero to 25 mg/cm$^2$/hour or more can be designed. The water-soluble glass is preferably a phosphate glass, and the silver may advantageously be introduced during manufacture as silver orthophosphate ($Ag_3PO_4$). The content of silver and other constituents in the glass can vary in accordance with conditions of use and desired rates of release, the content of silver generally being up to 10% by weight.

The glass may be formed by a number of methods. It may simply be cast by conventional or centrifugal procedures, or it may be prepared via one or more stages of rod, fibre or tube drawing. Other preparation techniques include foamed glass or comminution of the glass followed by pressing and sintering into a solid body. It may be presented for example as a solid body, a powder or granules of preselected size.

A preparation of this invention may comprise a composite material containing one or more than one water-soluble glass composition. The anti-microbial properties of the preparation of the invention are due entirely to the bacteriostatic properties of silver ions.

The antimicrobial properties of the preparation of the invention were demonstrated by placing a section of silver-containing water-soluble glass, cut from a 4 mm rod, in culture medium. Over a period of 36 hours the growth of *Pseudomonas aeruqinosa* was inhibited. A similar result was obtained when the culture medium was replaced with fluids recovered after use in Continuous Ambulatory Peritoneal Dialysis (CAPD). The inhibition of bacterial growth by slow release of silver has a wide range of application in those treatment where fluid enters or leaves the body by natural processes or by routes introduced by surgical intervention.

One such example exists in CAPD where patients with renal failure receive regular exchanges of dialysis fluid introduced into the peritoneal cavity. Delivery is carried out under aseptic conditions from an individual bottle or plastics bag of sterile dialysis fluid via a resident catheter in the lower abdomen. Each time the circuit is broken there is a risk of infection both at the implant site and in the peritoneum which can lead to episodes of peritonitis and also to the required removal of the implanted catheter. The interposing of silver-release glass at the connector sites, through which liquid entering or leaving the peritoneal cavity flows, offers a barrier to bacterial invasion.

Similarly, with parenteral infusions involving individual cannulae and catheters the incorporation of an anti-microbial barrier in accordance with this invention will reduce the risk to the patient.

The antimicrobial action of silver is known. One of the most widely used silver-based pharmaceutical compositions is silver sulphadiazine which is commonly used, in the form of an ointment, for the treatment of burn wounds, which are particularly subject to contamination by colonising organisms, especially bacterial and fungi, by topical application. In contact with the wound the silver sulphadiazine dissociates into silver ions and sulphadiazine, both components possessing antibiotic properties. The compound also exhibits some degree of slow or sustained release of the silver and sulphadiazine because of its relatively low aqueous solubility which, of course, retards the dissociation necessary for release of the antibiotic action. Silver nitrate and silver allantoinate are also used.

Figure 2A:
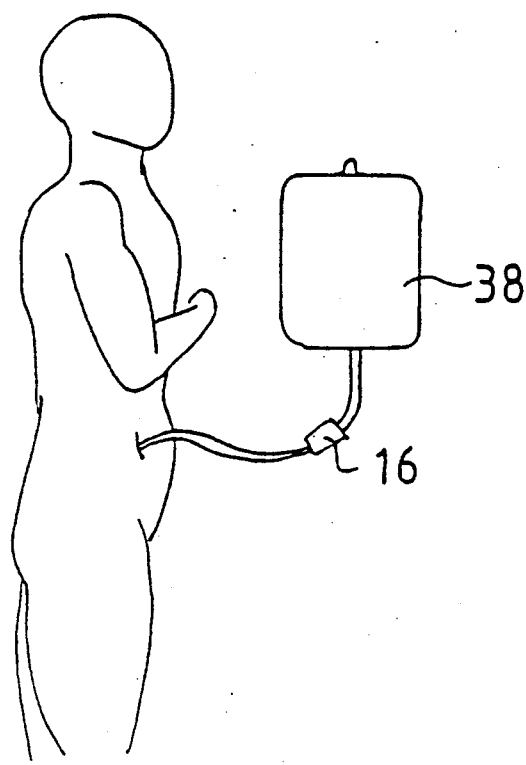
Figure 3:
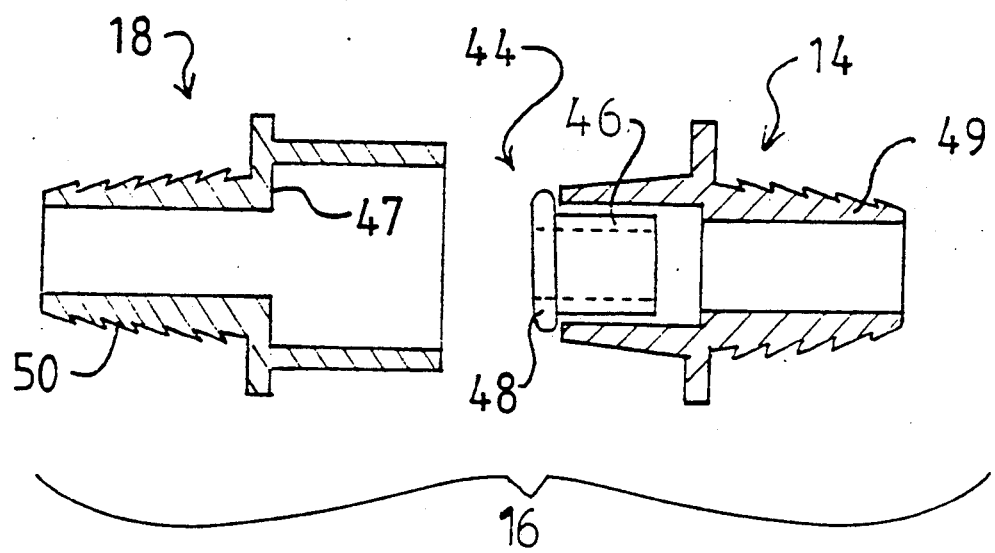

Embodiments of the present invention will now be described by way of example with reference to the accompanying drawings, in which:

FIG. 1 is a side view of apparatus of the present invention;

FIGS. 2(a) and (b) are side views of different forms of the apparatus of the invention in use; and FIG. 3 is a side sectional view of an alternative connection member of this invention.

Referring to FIG. 1, the apparatus of this embodiment of the invention comprises an indwelling urinary catheter 2 having inflatable balloon portions 4, 6 for maintaining the catheter in position in the urethra with the free end 8 in the bladder to collect urine through apertures 10, 12. At the outer end the catheter 2 terminates in a first portion 14 of a connector 16 whose second portion 18 leads to tubing 20 which enters a urine collection bottle 22. The bottle 22 has at its lower end remote from the tubing 20 a drain plug 24. The connection between the first and second portions 14, 18 of the connector represents a site of potential contamination by bacteria which can be introduced on releasing the connector 16, for example to change the bottle 22 and tubing 20.

The urine itself is contaminated and the bacteria can reproduce in the bottle 22 as the urine collects in it. Thus when a nurse empties the bottle 22 through the drain plug 24 there is a risk of bacteria being transferred to the nurse. Further, bacteria in the bottle 22 may find their way along the tubing 20, connector 16 and catheter 2 into the patient's bladder, causing infection.

In order to prevent such infection by bacterial reproduction and transfer, the first portion 18 of the connector 16 has a peripheral recess 26 defined by spaced shoulders 28, 30, and a sleeve or lining 32 of water-soluble glass impregnated with silver is retained in the recess 26 to form part of the flow passageway for urine through the connector. Further, the bottle 22 contains a braided pouch 34 within which are held granules of the impregnated water-soluble glass, the pouch being tubular and closed at each end. The material of the pouch 34 is such that it contains interstices which allow urine to pass through but which are small enough to prevent the granules of the glass escaping.

In use the glass sleeve 32 and the glass in the pouch 34 act as a bacteriostat preventing an increase in the number of bacteria in the urine itself and of bacteria introduced in the event of the connector 16 being opened, for example to change the bottle 22. This occurs by virtue of the gradual dissolution of the glass, releasing the silver with its bacteriostatic properties over a prolonged period. The composition of the glass determines the rate of silver release.

Figure 2B:
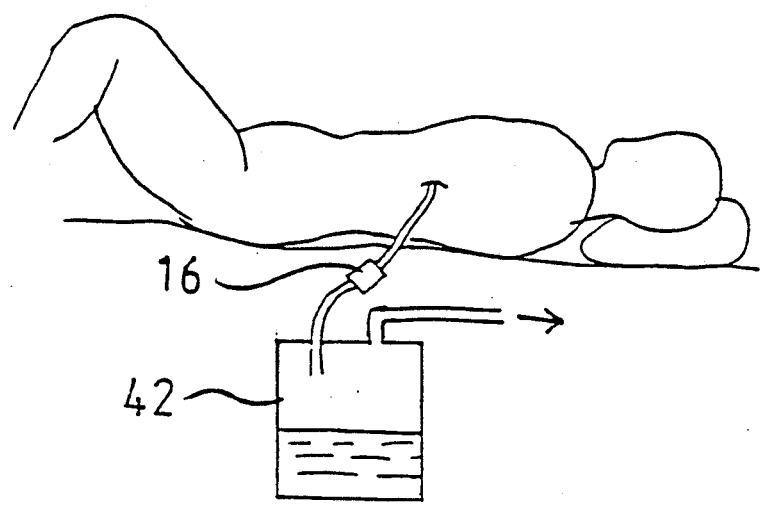

FIG. 2(a) illustrates the use of a connector 16, which is of similar construction to that shown in FIG. 1, in peritoneal dialysis in which fluid passes from a reservoir 38 into the peritoneum of the patient. In this case the fluid itself is sterile so the reservoir 38 need not contain a pouch 34 as in FIG. 1, but the sleeve 32 is required in the connector 16 to deal with bacteria which may be introduced when the connector is opened in order to replace the reservoir 38 when empty. FIG. 2(b) illustrates the apparatus in post-surgical drainage, in which suction is applied through a line 40 to the patient to draw fluid from the operation site into a collection bottle 42. Again, the connector 16 is of similar construction to that of FIG. 1 and includes the silver-impregnated sleeve 32.

Referring now to FIG. 3, the connector 16 has first and second portions 14, 18 having an ingot 44 of silver-contaminated water-soluble glass between them. The ingot 44 is in the form of a solid sleeve 46 having an annular flange 48 at one end to bear against an end face of the first portion 14 and a corresponding shoulder 47 on the second portion 18. The first and second portions 14, 18 each have a fitting 49, 50 for receiving an end portion of rubber tubing. The sleeve 46 fits within the first portion 14 so as to contact fluid passing through the connector 16.

In the connector of FIG. 3, the ingot 44 is made by mixing together 35 mole % of $NaH_2PO_4$, 15 mole % of $CaHPO_4$ and 50 mole % of $P_2O_5$, heating the mixture at 1050° C. for 20 minutes, and cooling and grinding the glass thus obtained until it forms a powder. This powder is then weighed and up to 10% by weight of silver orthophosphate ($Ag_3PO_4$) is added and mixed in. The mixture is then heated to 1050° C. to produce a homogeneous impregnated water-soluble glass, cast into shape and annealed.

The granulated form of the glass provided in the pouch 34 of FIG. 1 can also be made in this way, with a final granulation stage instead of casting.

Alternatively the silver orthophosphate can be included in the original mix to allow a single heating stage.

It has been found that if the silver-impregnated water-soluble glass used in these embodiments of the invention is heated directly at its surface after its manufacture, in a manner that creates a rapid temperature gradient through the material, elemental silver forms at the surface in a fine layer which in use provides an initial increased rate of dissolution of the silver into the fluid until the surface layer has all dissolved, after which the glass dissolves as normal with a slower rate of release of silver. In producing this effect it is important that the heating is not sustained after the formation of the silver surface layer as the glass otherwise devitrifies and the release rate of the silver becomes unpredictable.

Experiments using apparatus of the invention will now be described by way of example.

The silver-impregnated water-soluble glass was produced in two forms which would enable its incorporation into the urinary catheter collection system of FIG. 1 but using the connector shown in FIG. 3:

1. A silver-impregnated glass ingot inside a plastic connector which would be situated between the distal end of the catheter and the proximal end of the urine collection bag tubing. The reason for siting the silver glass here is that many episodes of urinary tract infection in catheterised patients are thought to result from contamination of the catheter/bag junction when the collection bag is disconnected and reconnected.

2. A porous plastic pouch containing small granules of silver-impregnated glass which would be situated inside the collection bag releasing silver ions into the collected urine. This would reduce the numbers of bacteria present in the collection bag which is thought to be a potential source of cross-infection in wards where there are several catheterised patients.

EXPERIMENT 1

Brain heart infusion broth containing small pellets of silver-impregnated glass were inoculated with small numbers of different test organisms and the broths incubated at 37° C. overnight. Test organisms used were
*Escherichia coli*
*Pseudomonas aeruqinosa*
*Proteus mirabilis*
*Klebsiella sp*
*Staphylococcus aureus*
*Staphylococcus epidermidis*
The broths were subcultured after 48 hours to assess whether bacterial growth had been inhibited or not. Control cultures were also set up which did not contain silver-impregnated glass pellets.

EXPERIMENT 2

Pooled samples of urine containing varying numbers of bacteria ranging from $1 \times 10^5$ to $1 \times 10^7$ organisms per ml of urine were run through the silver-impregnated glass ingot containing connector at the rate of 1 ml per minute (the approximate rate at which urine flows through a urinary catheter) for 2 hours. The number of organisms present in the urine before and after flowing through the connector and after incubation of the collected urine at room temperature for 24 hours were estimated. These were compared to the numbers of organisms present in similar samples of the pooled urine which had not been passed through the connector.

EXPERIMENT 3

Filtered (sterile) urine was run through the silver-impregnated glass connector at the rate of 1 ml per minute for 2 hours as before. The connector was then artificially contaminated with $1 \times 10^6$ organisms of *E. coli* and sterile urine run through the connector for a further 1 hour. This was to simulate contamination of the connector during changing of the collection bag. The numbers of organisms present in the collected urine was estimated immediately after collection (Time 0) and after 24, 48, 72, and 96 hours' incubation at room temperature.

This experiment was also carried out using nutrient broth instead of sterile urine (when urine was unavailable).

EXPERIMENT 4

Sterile urine was allowed to flow through the silver-impregnated glass connector at the rate of 1 ml per minute for 24 hours. Several samples were taken during this time for silver estimation in order to gain a picture of the rate of silver release into the collected urine.

EXPERIMENT 5

Filtered (sterile) urine was collected in a container containing silver-impregnated water-soluble glass granules in a braided plastic pouch. This urine was then artificially contaminated with a known number of organisms of *E. coli* and the collected urine incubated at room temperature for 4 days, the numbers of organisms present in the urine being estimated daily.

RESULTS

Preliminary experiments which assessed the ability of silver-impregnated glass to inhibit the growth of different types of bacteria showed that the glass pellets inhibited the growth of all types of bacteria except the *Proteus mirabilis*.

In Experiment 2, passing the urine through the connector did not immediately reduce the numbers of organisms present in the urine, but after 24 hours' incubation there was approximately a ten-fold reduction in the numbers of organisms in the urine which had been passed through the connector when compared with the control urine.

When sterile urine or nutrient broth was used and the connector artificially contaminated with *E. coli*, the numbers of organisms in the control urine had significantly multiplied after 24 hours' incubation, but the test urine which had been passed through the connector showed very small numbers of organisms present after 24 and 48 hours and regrowth of the *E. coli* did not occur until after 72 or 96 hours' incubation.

The preliminary results of the experiments assessing the use of the plastic pouch containing silver-impregnated glass granules to inhibit organism growth gave positive results.

Both the glass-containing connector and the plastic pouch containing glass granules released enough silver to inhibit the growth of bacteria and can be incorporated into urinary collection systems in order to reduce the risk of urinary tract infection in catheterised patients.

In the above Experiments the ingot contained in the connector comprised 35 mole % $NaH_2PO_4$, 15 mole % $CaHPO_4$ and 50 mole % $P_2O_5$, and 10% by weight of silver. This resulted in a rate of release of silver of 1 mg per $cm^2$ per hour.

The granules in the plastic pouch comprised 25 mole % $NaH_2PO_4$, 25 mole % $CaHPO_4$ and 50 mole % $P_2O_5$, with 5% by weight of silver. The silver release rate was 0.6 mg per $cm^2$ per hour.

In general, an increase in the amount of sodium present in the glass increases the rate of dissolution and therefore of silver release when the $P_2O_5$ content remains constant.

Modifications and improvements may be made without departing from the scope of the invention.

I claim:

1. Apparatus for antimicrobial use in passage of fluid to or from a living body, the apparatus comprising a conduit for insertion into the body, a reservoir for fluid and a connector member for connecting said conduit to said reservoir external of the body, wherein said connector member includes a water-soluble glass impregnated with elemental silver or a compound of silver, said water-soluble glass defining at least a part of a passageway for fluid to flow between the reservoir and the conduit.

2. Apparatus according to claim 1, wherein the connector member comprises a first portion having an end adapted for connection with said conduit and a second portion having an end adapted for connection with said reservoir, the first and second portions being releasably secured together to define a fluid passageway between the reservoir and the conduit and at least one of the first and second portions having an internal lining of said impregnated water-soluble glass.

3. Apparatus according to claim 2, wherein at least one of the first and second portions of the connector member has a pair of spaced shoulders between which said lining of impregnated water-soluble glass is retained.

4. Apparatus according to claim 1, 2 or 3, wherein the connector member comprises tubing having said impregnated water-soluble glass dispersed therein.

5. Apparatus according to claims 1, 2 or 3, wherein said reservoir contains water-soluble glass impregnated with elemental silver or a compound of silver.

6. Apparatus according to claim 5, wherein the impregnated water-soluble glass in the reservoir is disposed within an apertured container.

7. Apparatus according to claim 6, wherein the container is in the form of a flexible braided pouch having interstices through which liquid can pass.

8. Apparatus according to claims 1, 2, or 3, wherein the impregnated water-soluble glass is granular.

9. Apparatus according to claim 8, wherein the impregnated water-soluble glass has a surface layer of elemental silver.

10. A connector member having an inlet and an outlet and having walling defining a through passageway for flow of liquid from the inlet to the outlet, at least a part of said walling being formed of water-soluble glass impregnated with elemental silver or a compound of silver.

* * * * *